US00PP24747P3

(12) United States Plant Patent

Olesen et al.

(10) Patent No.: US PP24,747 P3

(45) Date of Patent: Aug. 12, 2014

(54) *CLEMATIS* PLANT NAMED 'EVIPO044'

(50) Latin Name: *Clematis cartmanii*
Varietal Denomination: Evipo044

(75) Inventors: Mogens Nyegaard Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 210 days.

(21) Appl. No.: 13/507,016

(22) Filed: May 31, 2012

(65) Prior Publication Data

US 2013/0326777 P1 Dec. 5, 2013

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Wendy C Haas

(57) ABSTRACT

A new *Clematis* plant with a compact growth habit, profuse, white flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

1 Drawing Sheet

Botanical classification: Genus: *Clematis*. Species: *cartmanii*.

Variety denomination: 'Evipo044'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 1995 and the resulting seeds were planted the following winter in a controlled environment in Guernsey, Channel Islands. The new variety named 'Evipo044' originated as a single seedling from the stated cross.

The new *clematis* plant may be distinguished from its female seed parent and male pollen parent primarily by flower size and compactness of growth habit.

The objective of the hybridization of this *clematis* plant was to create a new and distinct variety for nursery culture with unique qualities such as:

1. Uniform and abundant white flowers;
2. Vigorous and compact growth, making the variety suitable for container culture; and
3. Early flowering.

This combination of qualities was lacking in *clematis* plants that were in commercial cultivation and the qualities have been substantially achieved in the new variety.

'Evipo044' was selected by Mogens N. Olesen and Raymond J. Evison in their *clematis* development program in the Channel Islands, United Kingdom in 1996. Asexual reproduction of 'Evipo044' by means of vegetative cuttings and traditional layering was first performed by Mogens N. Olesen and Raymond J. Evison in the nursery during the summer of 1996. This initial and subsequent asexual propagations have demonstrated that the characteristics of 'Evipo044' are true to type and are transmitted from one generation to the next.

BRIEF DESCRIPTION OF THE DRAWING

The accompanying color illustration show as true as is reasonably possible to obtain in color photographs of this type the typical characteristics of the buds, flowers, leaves, and stems, of 'Evipo044'. Specifically illustrated in the drawing are flowers at various stages of development, flower in parts, leaves, and stems.

DETAILED DESCRIPTION OF THE VARIETY

The following is a detailed description of 'Evipo044', as observed in its growth throughout in a glasshouse located in Lancaster, Pa. Observed plants were cultivated for a period of 18 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of a non-patented *clematis* variety *Clematis*×*cartmanii* 'Joe' are compared to 'Evipo044' in Chart 1.

CHART 1

| | 'Evipo044' | 'Joe' |
|---|---|---|
| Flower diameter | 45 mm | 35 mm |
| Leaf morphology | Elliptic | Digitate |
| Tepal overlap | none | partial |

FLOWER AND FLOWER BUD

Blooming habit: Very early flowering in the season. Recurrent. The natural flowering period is from early April to September.

Flower bud:

*Size*.—Normally 18 mm in length. Bud diameter is 6 mm.

*Bud form*.—Tubular.

Peduncle:

*Surface texture*.—Smooth

*Length*.—On average 30 mm. .

*Color*.—Yellow-Green Group 144B.
*Strength*.—Moderately strong.

Receptacle:
*Surface texture*.—Smooth, lightly pubescent.
*Shape*.—Funnel.
*Size*.—2 mm (h)×2 mm (w).
*Color*.—Yellow-Green Group 144B.

Flower arrangement:
*Location on vine*.—Old growth.
*Borne*.—Normally in clusters of 15 to 25 flowers.

Flower bloom:
*Size*.—On average, flowers are 45 mm in diameter and 7 mm in depth.
*Profile*.—Open flowers are flat.
*Fragrance*.—None.
*Lasting quality*.—Flowers normally remain 7 days on the plant.

Tepals:
*Tepal color*.—The upper surface is White Group 155C. The lower surface is White Group 155C.
*Quantity*.—Normally 6 tepals.
*Size*.—22 mm in length by 8 mm wide.
*Shape*.—Individual tepal shape is lanceolate The tepal apex and base are acute.
*Apex recurvature*.—None.
*Tepal cross section*.—Flat.
*Margins*.—Entire.
*Persistence*.—Tepals drop away cleanly.

Reproductive organs:
*Arrangement*.—Female reproductive parts are tightly clustered and upright. Male parts are bearing at a 45 degee angle in a whorl around the pistils.
*Pollen*.—None observed.
*Anthers*.—Size: 1.5 mm in length. Color: White Group 155A. Quantity: On average.
*Filaments*.—Color: Yellow-Green Group 145C. Length: Yellow white.
*Pistils*.—Quantity: On average.
*Stigmas*.—Superior in location relative to the length of the filaments and the height of the anthers.
*Styles*.—Color: Green white. Length: mm.

Seed head characteristics: Not observed.

PLANT

Plant form: Climbing, trailing.
Plant growth: Moderately vigorous.
Size: Seasons growth attains 60 cm in height. Average spread is 40 cm.

Stems:
*Color*.—Juvenile stems are Yellow-Green Group 146C. Mature stems are Yellow-Green Group 146C with intonations of Greyed-Orange Group 174A.
*Internodes*.—On average, 60 mm between nodes.
*Length*.—Normally 15 cm from the base of the plant to the flowering portion of the stem.
*Diameter*.—Normally 2 mm.
*Texture*.—Mature stems are generally smooth.

Plant foliage:
*Leaf characteristics*.—Evergreen.
*Arrangement*.—Triternate.
*Leaf size*.—Compound leaves are normally 60 mm (l)× 55 mm (w). Leaflets are normally 40 mm (l)×30 mm (w).
*Abundance*.—On average 2 leaves per 10 cm of stem.
*Leaf color*.—Juvenile upper Yellow-Green Group 146A. Juvenile lower Yellow-Green Group 146B. Mature upper Yellow-Green Group 146A. Mature lower Yellow-Green Group 146B.
*Stipules*.—Absent.
*Petioles*.—Size: Normally 20 mm in length by 1.5 mm diameter. Texture: Smooth. Color: Yellow-Green Group 146A.
*Petioloule*.—Size: Normally 18 mm in length by 1 mm diameter. Texture: Smooth. Color: Yellow-Green Group 146A.
*Leaflet shape*.—Generally elliptic. The base is attenuate. The apex is rounded.
*Margin*.—Dentate to lobed.
*Surface*.—The upper side is smooth.
*Thickness*.—Thick.
*Glossiness*.—Glossy.

Disease resistance: Subject to any disease that normally attacks the species.

Cold hardiness: Trials to date show the variety is hardy to −10° C.

Heat tolerance: The variety has been found to be suitable for climate conditions found in the American Horticulture Society heat zone 7.

We claim:

1. A new and distinct variety of *clematis* plant named 'Evipo044', substantially as described and illustrated, due to its abundant white flowers, attractive long lasting foliage, compact growth, suitability for production from softwood cuttings in pots, and flowering under glasshouse conditions, which make the variety suitable for distribution in the floral industry.

* * * * *

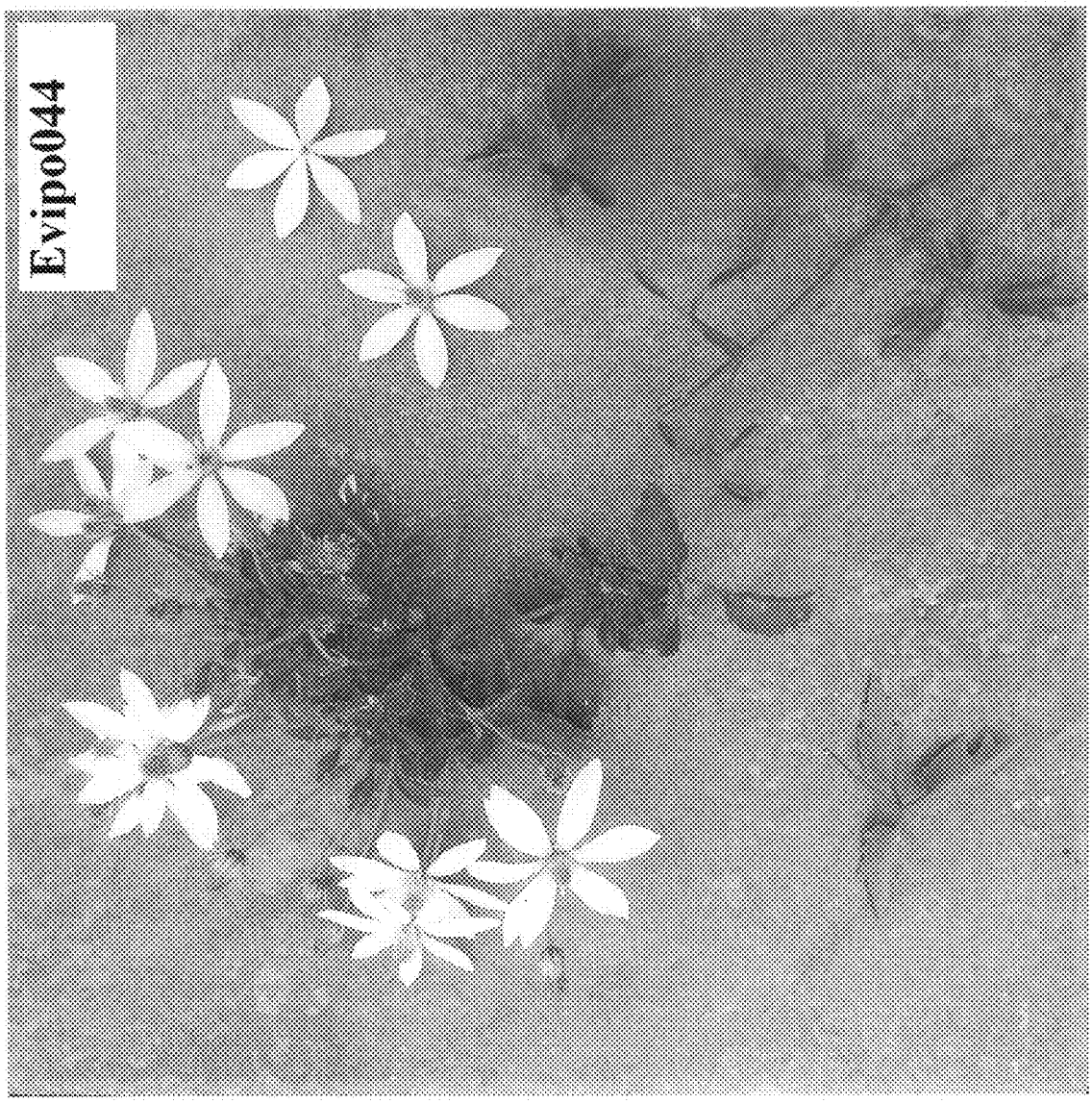
Evip0044